US00PP13020P2

(12) United States Plant Patent
Hoogendorn

(10) Patent No.: US PP13,020 P2
(45) Date of Patent: Oct. 1, 2002

(54) ALSTROEMERIA PLANT NAMED 'STALOG'

(75) Inventor: C. A. Hoogendorn, Aarlanderveen (NL)

(73) Assignee: Van Staaveren B.V., Aalsmeer (NL)

( * ) Notice: Subject to any disclaimer, the term of this patent is extended or adjusted under 35 U.S.C. 154(b) by 0 days.

(21) Appl. No.: 09/349,611

(22) Filed: Jul. 8, 1999

(51) Int. Cl.[7] ..... A01H 5/00

(52) U.S. Cl. ..... Plt./309

(58) Field of Search ..... Plt./309

(56) References Cited

PUBLICATIONS

UPOV–ROM GTITM Computer Database 2001/01, Feb. 6, 2001, GTI Jouve Retrieval Software, Citation for Alstroemeria 'Stalog'.*

The New Royal Horticultural Society Dictionary of Gardening, 1992, vol. 1, A to C, p. 141.

* cited by examiner

*Primary Examiner*—Bruce R. Campell
*Assistant Examiner*—June Hwu
(74) *Attorney, Agent, or Firm*—Christie, Parker & Hale, LLP

(57) ABSTRACT

A new and distinct Alstroemeria plant variety producing white flowers of good quality and attractive coloration.

1 Drawing Sheet

BACKGROUND OF THE INVENTION

The present invention relates to a new and distinct variety of Alstroemeria, family Alstroemeriaceae; genus Alstroemeria; specie Hybrid, which is a cross of 2 unnamed, undistributed seedlings; namely, 89W875-1 as seed parent and 87G1069-2 as pollen parent. The varietal denomination of the new variety is 'STALOG'.

Asexual reproduction by dividing rhizomes, and by tissue culture, through successive generations in Aalsmeer, The Netherlands, has demonstrated that the combination of characteristics as herein disclosed for 'Stalog' are firmly fixed and retained through successive generations.

SUMMARY OF THE INVENTION

The new variety of Alstroemeria, 'Stalog', produces white flowers of good quality.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of one year old plants of the new cultivar of Alstroemeria hybrid as observed in a greenhouse in Aalsmeer, The Netherlands. Color designations indicated are in accordance with The Royal Horticultural Society Colour Chart by color plate designations.

'Stalog' has not been observed under all possible environmental conditions, Phenotypic expression may vary with variations in environment such as temperature, light intensity, day length and growing and cultural conditions.

Botanical classification:
- *Family.*—Amaryllidaceae.
- *Genus.*—Alstroemeria sp.

- *Species.*—Hybrid between (*A. inodora*×*A. violacea*)×*A. aurea.*

PLANT

Form: Bush, upright.
Growth: Vigorous.
Height: About 160–200 cm.
Main stem: About 160–200 cm.
Branching characteristics: Flower stems do not branch.
Flower stem:
- *Length.*—About 160–200 cm.
- *Thickness.*—About 3–8 mm.
- *Color.*—Near 137A.

Foliage: Singly, not opposite, linear leaf venation, strong stems.
- *Quantity.*—Abundant.
- *Number of leaves.*—About 25–30.
- *Size of leaf.*—Length: About 10–15 cm. Width: About 2–4 cm.
- *Shape of leaf.*—Elliptic.
- *Margin.*—Minutely crimped.
- *Texture.*—Glossy.
- *Color.*—Upper side: Near 137A. Underside: Near 137C.
- *Stem color.*—Near 137A.
- *Rhizomes.*—Color: Near 155D. Size: About 10–25 cm.

THE BUD STAGE

Form: Pear-shaped.
Size:
- *Diameter.*—About 0.5–1 cm.
- *Length.*—About 1–2 cm.

Rate of opening: Fast, about 2–3 days.
Color of tepals when tepals begin to unfurl: Near 137C.

THE FLOWER STAGE

Blooming habit: Recurrent, year-round.
Flower:
- *Size.*—Moderate.
- *Diameter.*—About 5 to 6 cm.

*Depth.*—About 4 to 5 cm.
*Born.*—Singly born along branches in umbel.

Inflorescence:
*Shape.*—Umbel, flowers born singly along branches in umbel.

Peduncle:
*Length.*—About 7 to 15 cm.
*Color.*—Near 137C.
*Strength.*—Strong.
*Diameter.*—About 0.5 cm.
*Discoloration.*—No discoloration after full bloom.
*Florets per stem.*—About 3 to 5.
*Hairy.*—Not hairy.

Bloom:
*Type.*—Single.
*Form.*—Cup.
*Borne.*—Singly along simple racemes.
*Petalage.*—About 6.
*Shape of tepals.*—Inner tepals obovate, outer tepals obcordate.
*Arrangement.*—2 concentric circles of 3 tepals.
*Margin.*—Minute serration.
*Apex.*—Pointed.
*Size of bloom fully expanded.*—Diameter. About 5 to 6 cm. Depth: About 4 to 5 cm.
*Texture.*—Soft.
*Tepals fall off.*—Flower does not hang on and dry.
*Lasting quality.*—About 21 days on plant; about 14 days after cutting.
*Color.*—Outer tepals near 155D with a Green tip without stripes, inner tepals near 155D with a band or spot of Yellow near 7A around the center of petal with Brown stripes, same for reverse; outer tepals have Green tip near 137C; outer tepals have about 0 to 1 stripes, near 185A; inner lateral tepals near 13B; inner lateral tepals bear 20 to 30 spots near 185A; inner medial tepals have about 5 to 15 stripes near 185A.
*Point of tepal attachment.*—Near 155D.
*Discoloration as bloom ages.*—No discoloration.

Fragrance: None.

REPRODUCTIVE ORGANS

Stamen:
*Number.*—About 6.
*Color.*—Near 155D.
*Arrangement.*—Around the style.

Anthers:
*Size.*—About 0.5 to 1 cm.
*Color.*—Near 138A to 199A.

Filaments:
*Length.*—About 5 cm.
*Color.*—Near 155D.

Pollen:
*Quality.*—Good.
*Color.*—Near 152C.

Pistils: 1.
*Styles.*—Length about 4 cm.
*Color.*—Near 64C to about 155C.

Stigmas:
*Color.*—Near 13C.

Fertile: Sterile, no seeds.

Fruit:
*Shape.*—Round.
*Size.*—About 1–2 cm.
*Color at maturity.*—Near 164A.

Fruit type: Globular.
Fruit texture: 6 ribs.
Fruit size: About 1–2 cm.
Fruit color: Near 164A.

I claim:

1. A new and distinct Alstroemeria plant of the variety substantially as shown and described.

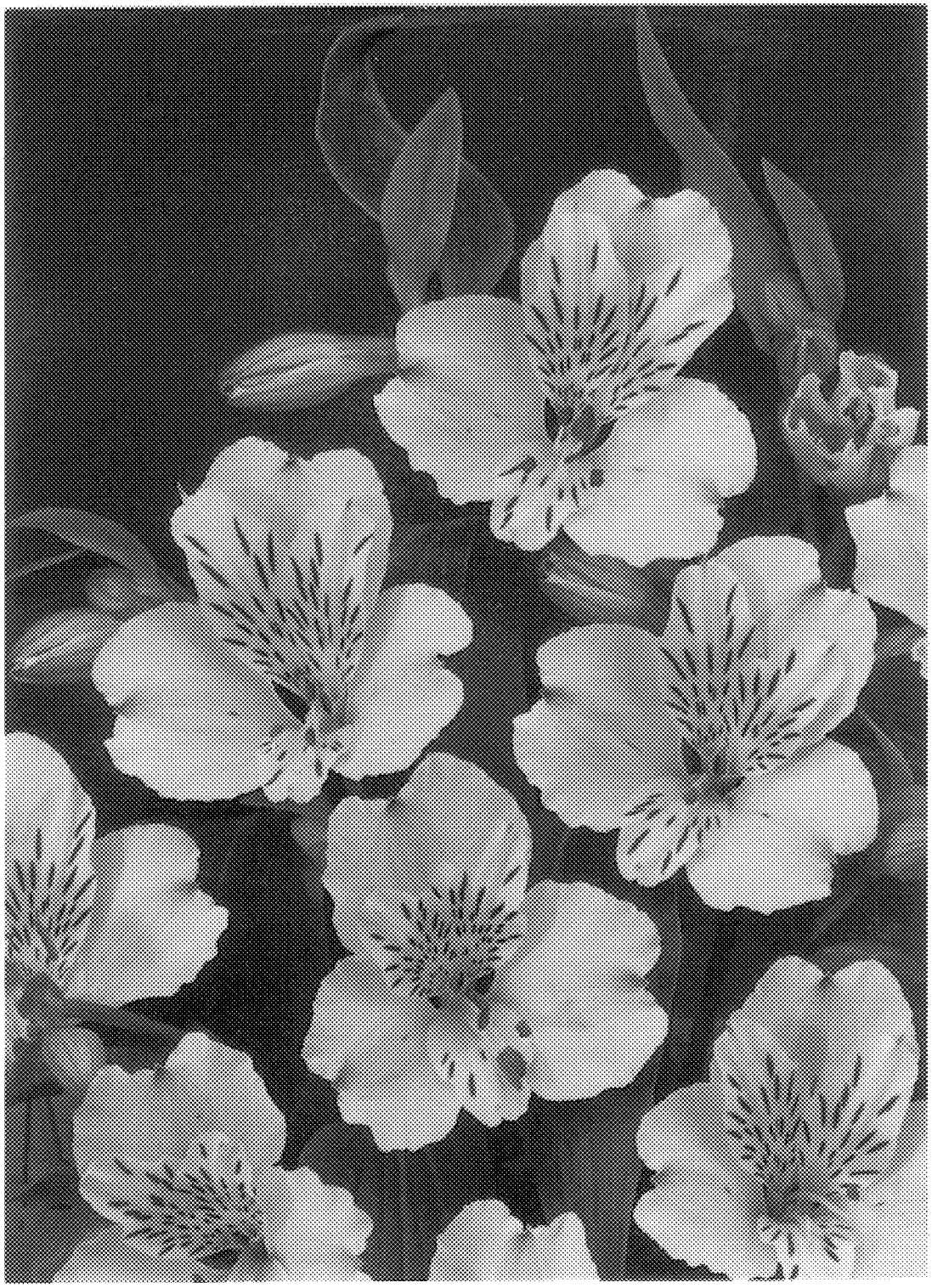

* * * * *